United States Patent
Bantia et al.

(10) Patent No.: US 11,110,092 B2
(45) Date of Patent: Sep. 7, 2021

(54) METHODS OF TREATING HEMATOLOGIC CANCERS

(71) Applicant: BIOCRYST PHARMACEUTICALS, INC, Durham, NC (US)

(72) Inventors: Shanta Bantia, Birmingham, AL (US); Philip Breitfeld, Birmingham, AL (US); Yarlagadda S Babu, Birmingham, AL (US)

(73) Assignee: BIOCRYST PHARMACEUTICALS, INC., Durham, NC (US)

( * ) Notice: Subject to any disclaimer, the term of this patent is extended or adjusted under 35 U.S.C. 154(b) by 26 days.

(21) Appl. No.: 16/400,414

(22) Filed: May 1, 2019

(65) Prior Publication Data
US 2019/0255058 A1  Aug. 22, 2019

Related U.S. Application Data

(60) Division of application No. 14/190,987, filed on Feb. 26, 2014, now abandoned, which is a continuation of application No. 12/747,456, filed as application No. PCT/US2008/086256 on Dec. 10, 2008, now abandoned.

(60) Provisional application No. 61/012,762, filed on Dec. 10, 2007.

(51) Int. Cl.
| | |
|---|---|
| A61K 31/519 | (2006.01) |
| A61K 31/4184 | (2006.01) |
| A61P 35/02 | (2006.01) |
| A61P 35/00 | (2006.01) |
| A61K 39/395 | (2006.01) |
| A61K 31/7076 | (2006.01) |
| C07K 16/28 | (2006.01) |
| A61K 45/06 | (2006.01) |
| A61K 39/00 | (2006.01) |

(52) U.S. Cl.
CPC ........ *A61K 31/519* (2013.01); *A61K 31/4184* (2013.01); *A61K 31/7076* (2013.01); *A61K 39/39541* (2013.01); *A61K 39/39558* (2013.01); *A61P 35/00* (2018.01); *A61P 35/02* (2018.01); *C07K 16/2887* (2013.01); *A61K 39/3955* (2013.01); *A61K 45/06* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 5,595,721 | A | 1/1997 | Kaminski |
| 6,090,365 | A | 7/2000 | Kaminski |
| 8,206,711 | B2 | 6/2012 | White |
| 2001/0053784 | A1* | 12/2001 | Morris, Jr. .......... C07D 403/04 514/300 |

FOREIGN PATENT DOCUMENTS

| | | |
|---|---|---|
| WO | 9611200 | 4/1996 |
| WO | 0027428 | 5/2000 |
| WO | 2003097052 | 11/2003 |
| WO | 2007002931 | 1/2007 |
| WO | 2007113648 | 11/2007 |

OTHER PUBLICATIONS

Roue et al., "Activity of Bendamustine (TREANDA™) in Chronic Lymphocytic Leukemia and Mantle Cell Lymphoma Cells with Alterations in DNA Damage Response Pathway" Blood vol. 108 No. 11 p. 2510 (Year: 2006).*
Surget et al., "Bendamustine and melphalan kill myeloma cells similarly through reactive oxygen species production and activation of the p53 pathway and do not overcome resistance to each other" Leukemia and Lymphoma, Sep. 2014, vol. 55 No. 9 pp. 2165-2173 (Year: 2014).*
Balakrishnan, et al., "Forodesine, an inhibitor of purine nucleoside phosphorylase, induces apoptosis in chronic lymphocytic leukemia cells" Blood; 2006, 108: 2392-2398.
Rummel, et al., "Bendamustine Plus Rituximab is Effective and Has a Favorable Toxicity Profile in the Treatment of Mantle Cell and Low-Grade Non-Hodkin's Lymphoma" J Clin Oncol; vol. 23, No. 15, May 20, 2005; pp. 3383-3389.
Alonso, et al., "The Purine Nucleoside Phosporylase Inhibitor Forodesine (BXC-1777) is a Potent Cytotoxic Agent and Has Synergistic Activity with Bendamustine in Chronic Lymphocytic Leukemia (CLL) Irrespective of ZAP-70 Levels and p53 Status" Blood (ASH Annual Meeting Abstracts) 2007 110: Abstract 3122.
Cheson, Bruce D., "Clinical Management of T-Cell Malignancies: Current Perspectives, Key Issues and Emerging Therapies" Semin Oncol 34 (Suppl. 5): S3-S7; 2007.
Carde, P., "Actualites de l'ASCO 2007" Oncologie, vol. 9; Oct. 14, 2007; pp. 735-738.
Jeha, Sima, "New Therapeutic Strategies in Acute Lymphoblastic Leukemia" Seminars in Hematology; vol. 46, No. 1; Jan. 2009; pp. 76-88.

(Continued)

*Primary Examiner* — Eric Olson
(74) *Attorney, Agent, or Firm* — Maynard Cooper & Gale, P.C.; Matthew J. Parker

(57) ABSTRACT

The present application relates to treatment of hematologic cancers, which treatments can include, e.g., administration of a purine nucleoside phosphorylase (PNP) inhibitor, an alkylating agent and/or an anti-CD20 agent, and related compositions and kits.

6 Claims, 8 Drawing Sheets

(56) References Cited

OTHER PUBLICATIONS

Lissitchkov, et al., "Phase-I/II study to evaluate dose limiting toxicity, maximum tolerated dose, and tolerability of bendamustine HCI in pre-treated patients with B-chronic lymphocytic leukemia (Binet stages B and C) requiring therapy" J. Cancer Res Clin Oncol (2006) 132: 99-104.

Merup, Mats, et al., "6q Deletions in Acute Lymphoblastic Leukemia and Non-Hodgkin's Lymphomas" Blood, vol. 91, No. 9; May 1, 1998; pp. 3397-3400.

Murch, Lisa, "American Society of Hematology—47th Annual Meeting and Exposition Dec. 10-13, 2005, Atlanta, GA, USA" IDrugs 2006 9(2): 84-86.

Robak, T., et al., "Purine Nucleoside Analogues for the Treatment of Hematological Malignancies: Pharmacology and Clinical Applications" Current Cancer Drug Targets, 2005, 5, pp. 421-444.

Herold, M., et al., "Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19)" J Cancer Res Clin Oncol (2006) 132: 105-112.

Rummel, et al., "Bendamustine in the Treatment of Non-Hodgkin's Lymphoma: Results and Future Perspectives" Seminars in Oncology, vol. 29, No. 4, Suppl 13 Aug. 2002: pp. 27-32.

Duvic, Madeleine, "Systemic Monotherapy vs Combination Therapy for CTCL: Rationale and Future Strategies" Oncology Journal, Review Article, Feb. 1, 2007: pp. 1-7.

Bergmann, et al., "Efficacy of bendamustine in patients with relapsed or refractory chronic lymphocytic leukemia: results of a phase I/II study of the German CLL Study Group" Chronic Lymphoproliferative Disorders—Research Paper; Haematologica 2005; 90: pp. 1357-1364.

Galmarini, Carlo, "Drug evaluation: Forodesine—a PNP inhibitor for the treatment of leukemia, lymphoma and solid tumor" IDrugs 2006 9(10): 712-722.

Aivado, et al., "Bendamustine in the Treatment of Chronic Lymphocytic Leukemia: Results and Future Perspectives" Seminars in Oncology, vol. 29, No. 4; Suppl 13 Aug. 2002: pp. 19-22.

\* cited by examiner

| CLL #<br>% ZAP-70 | ATM STATUS | 12 trisomy (% of cells) | 13q deletion (% of cells) | PREVIOUS TREATMENT | RESPONSE TO PREVIOUS TREATMENT | FORODESINE CYTOTOXICITY (2 μM+dGuo 20 μM) | BENDAMUSTINE CYTOTOXICITY (25 μM) | FLUDARABINE CYTOTOXICITY (1 μg/ml (7.5 μM) |
|---|---|---|---|---|---|---|---|---|
| #7 60% | Normal | Normal | 11.4 % | CdA / FCM | YES | 87.2 ±3% | 12.5 ±4% | 2.1 ±2% |
| #28 1% | Normal | Normal | Normal | FC / R-F / CHOP | NO | 77.1 ±5% | 41.8 ±2% | 43.3 ±3% |
| #8 53% | Normal | Normal | 90% | - | - | 77.9 ±2% | 40.6 ±2% | 31.1 ±2% |
| #2 91% | Normal | 45 % | Normal | FCM | YES | 78.2 ±2% | 65.2 ±1% | 59.2 ±4% |
| #25 3% | Normal | Normal | 5% | CLB | NO | 68.3 ±4% | 25.9 ±3% | 25.9 ±3% |
| #9 50% | Normal | Normal | Normal | R-CHOP | NO | 63.1 ±6% | n.d. | n.d. |
| #12 36% | Normal | Normal | 29% | - | - | 66.1 ±3% | 26.47 ±5% | 42.65 ±2% |
| #4 73% | n.d. | n.d. | n.d. | FCM / CHOP | NO | 46.7 ±4% | 52.7 ±4% | 50.1 ±4% |
| #22 n.d. | Normal | Normal | Normal | - | - | 46.5 ±2% | 5.8 ±3% | 1.1 ±2% |
| #21 7% | Normal | 30.5 % | Normal | CHOP / R-CHOP | NO | 33.4 ±3%** | 38.3 ±3% | 40.1± 2% |
| #3 87% | Normal | Normal | 90% | FCM/Camp/PDN | NO | 20.1 ±5%** | 19.2 ±2% | 27.3 ±5% |
| | | | | | MEAN ±SD | 60.4 ±21% | 32.8 ±34% | 33.3 ±36% |

FIG. 3

| Combination Index for Forodesine/Bendamustine (48h) | | | | | | | | | |
|---|---|---|---|---|---|---|---|---|---|
| CLL | % ZAP-70 | For 2+10 Bend 10 | For 2+10 Bend 25 | For 2+20 Bend 10 | For 2+20 Bend 25 | CLL | % ZAP-70 | For 2+10 Bend 10 | For 2+10 Bend 25 | For 2+20 Bend 10 | For 2+20 Bend 25 |
| #24 | 2% | 0.70 | 1.05 | 0.52 | 0.44 | #6 | 30% | 1.11 | 0.36 | 0.73 | 0.46 |
| #19 | 12% | 0.53 | 0.83 | 0.36 | 0.61 | #100 | 100% | 0.77 | 0.82 | 0.90 | 0.80 |
| #23 | 0.4% | 0.94 | 0.52 | 0.40 | 0.50 | #74 | 64% | 0.70 | 0.79 | 0.76 | 0.55 |
| #20 | 19% | 0.54 | 0.64 | 0.81 | 0.82 | #42 | 72% | 0.93 | 0.73 | 0.71 | 0.75 |
| #27 | 3% | 0.56 | 0.57 | 0.45 | 0.46 | #18 | 29% | 0.14 | 0.04 | 0.1 | 0.04 |
| #21 | 4% | 0.26 | 0.50 | 0.10 | 0.24 | #17 | 41% | 1.02 | 1.10 | 0.98 | 1.10 |
| #12 | 10% | 0.65 | 0.28 | 0.59 | 0.34 | #10 | 30% | 0.51 | 0.49 | 0.27 | 0.20 |
| #15 | 25% | 0.63 | 0.59 | 0.25 | 0.19 | #36 | 42% | 0.35 | 0.51 | 0.29 | 0.26 |
| #50 | 1% | 0.31 | 0.27 | 0.46 | 0.43 | #16 | 32% | 0.85 | 0.83 | 0.30 | 0.27 |
| ZAP-70$^{Low}$ MEAN CI | | 0.51 | 0.52 | 0.39 | 0.40 | ZAP-70$^{High}$ MEAN CI | | 0.63 | 0.56 | 0.50 | 0.44 |

FIG. 5A

Combination index (CI) < 1 is indicative of synergism (Chou & Talalay's method).

| Combinations analyzed: | CLL #3 | #74 | #1 | #87 | #42 | #6 | #92 |
|---|---|---|---|---|---|---|---|
| Rituximab 25 + Forod 2 + dGuo10: | 0.64 | 0.73 | 0.59 | 0.13 | 0.88 | 0.46 | 0.72 |
| Rituximab 50 + Forod 2 + dGuo10: | 0.56 | 0.72 | 0.76 | 0.13 | 0.52 | 0.74 | 0.77 |
| Rituximab 25 + Forod 2 + dGuo20: | 0.51 | 0.55 | 0.49 | 0.12 | 0.63 | 0.35 | 0.60 |
| Rituximab 50 + Forod 2 + dGuo20: | | | | | | | |

Combination Index    CI mean = 0.53

FIG. 6

METHODS OF TREATING HEMATOLOGIC CANCERS

CROSS-REFERENCE TO RELATED APPLICATIONS

This application is a division of U.S. application Ser. No. 14/190,987, filed Feb. 26, 2014. U.S. application Ser. No. 14/190,987 is a continuation of U.S. application Ser. No. 12/747,456, filed on Sep. 28, 2010. U.S. application Ser. No. 12/747,456 is a national stage under 35 U.S.C. § 371 of International Application PCT/US08/86256, filed on Dec. 10, 2008. International Application PCT/US08/8256 is entitled under 35 U.S.C. § 119(e) to the benefit of the filing date of provisional U.S. Patent Application 61/012,762, filed on Dec. 10, 2007.

TECHNICAL FIELD

This application relates to the treatment of hematologic cancers, for example, cancers of the blood, by methods that include administration of a purine nucleoside phosphorylase (PNP) inhibitor. In particular, methods of treating chronic lymphocytic leukemia (CLL) and acute lymphocytic leukemia (ALL) are described.

BACKGROUND

Cancer is now the second leading cause of death in the United States and over 8,000,000 persons in the United States have been diagnosed with cancer. In 1995, cancer accounted for 23.3% of all deaths in the United States (see, e.g., U.S. Dept. of Health and Human Services, National Center for Health Statistics, Health United States 1996-97 and Injury Chartbook 117 (1997)).

Cancer is now primarily treated with one or a combination of three types of therapies: surgery; radiation; and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death. Thus, more effective cancer treatments are needed.

SUMMARY

Provided herein is a method of treating a hematologic cancer (e.g., CLL and ALL) in a subject. The method includes the steps of: (a) administering to the subject an effective amount of a purine nucleoside phosphorylase (PNP) inhibitor; and (b) administering to the subject an effective amount of an alkylating agent or an anti-CD20 agent. In certain embodiments, the PNP inhibitor is Forodesine. In other embodiments, the alkylating agent is selected from a mustard derivative, a nitrosourea derivative, a platinum compound, and an imidazole carboxamide compound. In some embodiments, the alkylating agent is Bendamustine. In certain embodiments, the anti-CD20 agent is Rituximab.

In some embodiments, the PNP inhibitor and alkylating agent or anti-CD20 agent are administered concurrently, while in other embodiments, the PNP inhibitor and alkylating agent or anti-CD20 agent are administered sequentially. In the latter embodiment, the alkylating agent or anti-CD20 agent can be administered one or more times prior to administration of the PNP inhibitor.

In another embodiment, a method of treating a hematologic cancer in a subject resistant to one or more chemotherapeutic agents (e.g., an alkylating agent such as Bendamustine and a purine nucleoside analogue such as Fluradabine) can include the steps of: (a) identifying a subject resistant to one or more chemotherapeutic agents; and (b) administering to the subject a PNP inhibitor. In specific embodiments, the PNP inhibitor is Forodesine.

In other embodiments, a method of treating a subject with a hematologic cancer can include the steps of: (a) detecting a p53 deletion in one or more cancer cells in a sample from the subject; and (b) administering to the subject a PNP inhibitor. In certain embodiments, the PNP inhibitor is Forodesine. In some embodiments, the method can further include detecting the presence of a 17p deletion, and/or determining if one or more cancer cells in the sample are resistant to one or more chemotherapeutic agents (e.g., an alkylating agent and a purine nucleoside analogue).

Further provided herein is a pharmaceutical composition comprising a PNP inhibitor and an alkylating agent or an anti-CD20 agent.

Also provided herein is a kit comprising a PNP inhibitor and an alkylating agent or an anti-CD20 agent. In some embodiments, the kit can further include a delivery system for the PNP inhibitor, the alkylating agent, the anti-CD20 agent, or any combination thereof. In another embodiment, the kit can also include instructions for treating a subject.

In another embodiment, a kit comprises a PNP inhibitor. In one embodiment, the kit further includes a label that indicates that the contents are to be administered to a subject that is resistant to an alkylating agent. In some embodiments, the kit also includes a label that indicates that the contents are to be administered to a subject with a p53 deletion. In a final embodiment, the kit can include a label that indicates that the contents are to be administered with an alkylating agent or an anti-CD20 agent.

Certain embodiments provide the use of a purine nucleoside phosphorylase (PNP) inhibitor and an alkylating agent to prepare a medicament useful for treating a hematologic cancer in an animal.

Certain embodiments provide the use of a purine nucleoside phosphorylase (PNP) inhibitor and an anti-CD20 agent to prepare a medicament useful for treating a hematologic cancer in an animal.

Certain embodiments provide the use of a purine nucleoside phosphorylase (PNP) inhibitor and an alkylating agent for treating a hematologic cancer.

Certain embodiments provide the use of a purine nucleoside phosphorylase (PNP) inhibitor and an anti-CD20 agent for treating a hematologic cancer.

The details of one or more embodiments of the invention are set forth in the accompanying drawings and the description below. Other features, objects, and advantages will be apparent from the description and drawings, and from the claims.

DESCRIPTION OF DRAWINGS

FIG. 3 displays values detailing the p53 deleted CLL cases having a high response to Forodesine.

FIGS. 5A and 5B displays the combination index data for Forodesine/Bendamustine and Forodesine/Fludarabine.

FIG. 6 details the combination index data for Forodesine/Rituximab.

DETAILED DESCRIPTION

Figure 1A:
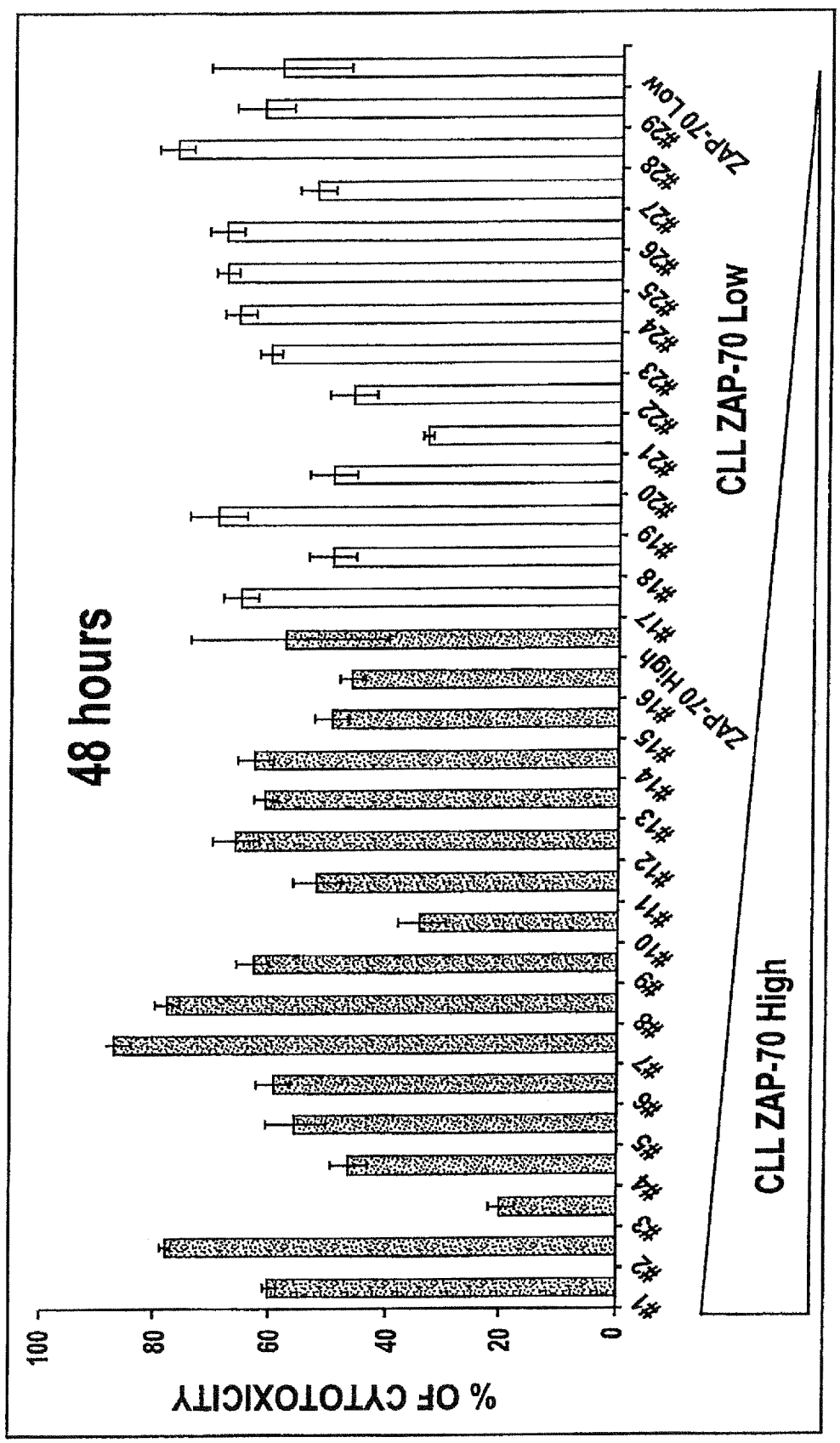
FIGS. 1A and 1B details the cytotoxicity effect of Forodesine in CLL cells exhibiting both high and low ZAP-70 levels.

As described herein, treatment with forodesine induced time and dose-dependent cell death in primary CLL cells. A cytotoxic response higher than 60% with forodesine 2 µM and dGuo 20 µM was observed in 48% of the cases, and in only 9% of cases was the cytotoxicity was lower than 40%. No differences in the response was observed regarding genetic abnormalities, such as deletions in 17p13 (TP53) and 11q22-q23 (ATM), genetic abnormalities acquired in advanced disease and associated with drug resistance and short survival of CLL patients. Those CLL cases with p53 or 11q alterations displayed a high sensitivity to forodesine (mean cytotoxicity 60.1% at 48 hours), with good cytotoxic response achieved in chemorefractory CLL patients. The combination of forodesine with clinical anti-leukemic regimens enhanced in vitro cytotoxic responses, with a strong synergistic effect observed with the combination of forodesine and low doses of bendamustine, the monoclonal antibody anti-CD20 rituximab or cyclophosphamide. In contrast, an antagonistic effect was found with fludarabine. Therefore, forodesine represents a novel chemotherapeutic approach able to induce apoptosis of CLL cells bypassing the ATM/p53 pathway.

Accordingly, certain embodiments provide methods of treating a hematologic cancer in a subject comprising the steps of administering to the subject an effective amount of a purine nucleoside phosphorylase (PNP) inhibitor; and administering to the subject an effective amount of an alkylating agent or an anti-CD20 agent.

In certain embodiments, the PNP inhibitor is Forodesine.

In certain embodiments, the alkylating agent is selected from a mustard derivative, a nitrosourea derivative, a platinum compound, and an imidazole carboxamide compound.

In certain embodiments, the alkylating agent is a mustard derivative. In certain embodiments, the alkylating agent is Bendamustine.

In certain embodiments, the anti-CD20 agent is Rituximab.

In certain embodiments, the PNP inhibitor and alkylating agent or anti-CD20 agent are administered concurrently.

In certain embodiments, the PNP inhibitor and alkylating agent or anti-CD20 agent are administered sequentially.

In certain embodiments, the alkylating agent or anti-CD20 agent is administered one or more times prior to administration of the PNP inhibitor.

In certain embodiments, the hematologic cancer is selected from chronic lymphocytic leukemia and acute lymphoblastic leukemia.

In certain embodiments, the hematologic cancer is chronic lymphocytic leukemia.

In certain embodiments, the hematologic cancer is acute lymphoblastic leukemia.

In certain embodiments, an effective amount of an alkylating agent is administered to the subject.

In certain embodiments, an effective amount of an anti-CD20 agent is administered to the subject.

In certain embodiments of the methods, the methods comprise administering to the subject an effective amount of a PNP inhibitor, an effective amount of an alkylating agent, and an effective amount of an anti-CD20 agent.

In certain embodiments, the PNP inhibitor, alkylating agent and anti-CD20 agent are administered concurrently.

In certain embodiments, the PNP inhibitor, alkylating agent and anti-CD20 agent are administered sequentially.

In certain embodiments, the alkylating agent and anti-CD20 agents are administered one or more times prior to administration of the PNP inhibitor.

Certain embodiments provide methods of treating a hematologic cancer in a subject resistant to one or more chemotherapeutic agents comprising the steps of identifying a subject resistant to one or more chemotherapeutic agents; and administering to the subject a PNP inhibitor.

In certain embodiments, the subject is resistant to one or more chemotherapeutic agents selected from the group consisting of an alkylating agent and a purine nucleoside analogue.

In certain embodiments, the alkylating agent is Bendamustine.

In certain embodiments, the purine nucleoside analogue is Fluradadine.

Certain embodiments provide methods of treating a subject with a hematologic cancer comprising the steps of detecting a p53 deletion in one or more cancer cells in a sample from the subject; and administering to the subject a PNP inhibitor.

In certain embodiments, the methods can further comprise detecting the presence of a 17p deletion.

In certain embodiments, the methods can further comprise determining if one or more cancer cells in the sample are resistant to one or more chemotherapeutic agents.

In certain embodiments, the cancer cell or cells are resistant to one or more chemotherapeutic agents selected from the group consisting of an alkylating agent and a purine nucleoside analogue.

Certain embodiments provide pharmaceutical compositions comprising a PNP inhibitor and an alkylating agent or an anti-CD20 agent.

In certain embodiments, the composition comprises Forodesine and Bendamustine.

In certain embodiments, the composition comprises Forodesine and Rituximab.

In certain embodiments, the composition comprises a PNP inhibitor, an alkylating agent, and an anti-CD20 agent.

In certain embodiments, the composition comprises Forodesine, Bendamustine and Rituximab.

Certain embodiments provide kits comprising a PNP inhibitor and an alkylating agent or an anti-CD20 agent.

In certain embodiments, the kits can further comprise a delivery system for the PNP inhibitor, the alkylating agent, the anti-CD20 agent, or any combination thereof.

In certain embodiments, the kits can further comprise instructions for treating a subject.

In certain embodiments, the kits comprise a PNP inhibitor and an alkylating agent.

In certain embodiments, the kits comprise a PNP inhibitor and an anti-CD20 agent.

In certain embodiments, the kits comprise Forodesine and Bendamustine. In certain embodiments, the kits comprise Forodesine and Rituximab.

In certain embodiments, the kits comprise a PNP inhibitor, an alkylating agent, and an anti-CD20 agent.

In certain embodiments, the kits comprise Forodesine, Bendamustine and Rituximab.

Certain embodiments provide kits that comprise a PNP inhibitor.

In certain embodiments, the kits comprise a label that indicates that the contents are to be administered to a subject that is resistant to an alkylating agent.

In certain embodiments, the kits further comprise a label that indicates that the contents are to be administered to a subject with a p53 deletion.

In certain embodiments, the kits further comprise a label that indicates that the contents are to be administered with an alkylating agent or an anti-CD20 agent.

Unlike others nucleoside analogs, forodesine is not incorporated to DNA. Forodesine treatment leads to a dGTP increase in CLL cells, and this increase correlated with cell cytotoxicity, indicating that the dGTP levels reached after forodesine treatment would be a surrogate marker indicative of the cytotoxic response. The susceptibility of CLL to forodesine may be due to the high dCK activity observed in this cells, activity positively regulated by the phosphorylation of dCK on Ser-74. A significant positive correlation was observed between phospho-dCK/dCK ratio and forodesine-induced apoptosis. dCK also catalyzes the phosphorylation required for the activation of several anti-leukemic nucleoside analogues, such as fludarabine, gemcitabine or cladribine. The antagonic effect observed between forodesine and fludarabine can be explained by the reduction on dGTP levels observed after combination of fludarabine with forodesine. These results indicate that dCK phosphorylation and the subsequent increase in dGTP play an important role as first steps to apoptosis induction by forodesine in CLL cells.

Several mechanisms for dGTP-mediated cell death have been proposed. For example, accumulated deoxynucleosides can be phosphorylated in the mitochondria by deoxyguanosin kinase and thymidine kinase, leading to abnormal accumulation of dNTPs that might interfere with mitochondrial DNA synthesis and repair, giving to increased sensitivity to mitochondrial damage, p53 activation and apoptosis. The imbalance in mitochondrial dGTP could also affect mitochondrial ATP synthesis and/or inactivation of antioxidants enzymes of the mitochondrial electron transport chain, leading to ROS production. Mitochondrial genome is highly sensitive to oxidative stress damage that may rapidly initiate apoptosis. As described herein, forodesine activated the mitochondrial apoptotic pathway by production of ROS and $\Delta\Psi m$ loss, leading to caspase-dependent and independent apoptosis. ROS are generated by the mitochondrial electron transport, and under severe oxidative stress the increase in $O_2^-$, $OH^-$ or $H_2O_2$ levels provoke loss of $\Delta\Psi m$ and cell death. These events induced by forodesine were reverted by pre-incubation of CLL cells with Tiron and NAC, specific scavengers of $O_2^-$, which supports a role of oxidative stress preceding the activation of mitochondrial apoptotic pathway. Phosphorylation and activation of p53 is induced by the DNA damage response, but also by several stress signals. Superoxide overproduction and subsequent induction of DNA damage can induce apoptosis by activating ROS-mediated mitochondrial pathway and p53 activation. In this sense, ROS generation induced by forodesine may act as an upstream regulator of p53 activation. Described herein are results that demonstrate p53 stabilization in wild type p53 CLL cases, and also that forodesine activated the mitochondrial apoptotic pathway in cases with p53 alterations, indicating that forodesine acts by a different and/or additional mechanism independent of p53. Oxidative stress and ROS production leads also to activation of the transcription factor E2F-1, which regulates both p53 dependent as well independent apoptosis through different pathways. E2F-1 increases p53 phosphorylation at residues that are also phosphorylated in response to DNA damage, but also is able to induce cell death by activation of the p53 homologue p73 via a p53-independent apoptotic pathway. How ROS generation can regulate E2F-1, p53 and/or p73 activation and cell death remains poorly understood.

An early event of the mitochondrial apoptotic pathway is the formation of the apoptosome and activation of caspase-9, which cleaves and activates caspase-3 as well caspase-8. Forodesine induced a time-related activation of caspase-9 and -3, as well pro-caspase-8 simultaneously to caspase-9 activation. In turn caspase-8 induced the cleavage of BID protein to its pro-apoptotic truncated form, that activates mitochondrial apoptotic pathway. Selective inhibition of caspase-8 reduced $\Delta\Psi m$ loss induced by forodesine, but the effect on cell death at later times was moderated, suggesting that caspase-8/BID lead to the amplification loop of the mitochondrial apoptotic pathway. Caspase-9 activation could be not enough per sec to induce apoptosis, so the activation of caspase-8/BID together with the decrease in the inhibitors of apoptosis XIAP and survivin would increase caspase-9 and -3 activities, and therefore potentiates apoptosis induced by forodesine.

The BCL-2 family of proteins controls the commitment to apoptotic cell death. A balance between pro-survival such as BCL-2 and MCL-1 and pro-apoptotic BCL-2 members (BAX, BAK and the BH3-only proteins BIM, PUMA, NOXA, BAD, BID, BMF, BIK and HRK) controls the outcome of many death signaling pathways. In CLL patients, high levels of BCL-2 and MCL-1 correlate with disease progression, poor survival and the failure to achieve complete response to therapy with alkylating agents, nucleosides analogues and rituximab. Forodesine induced the accumulation BIM protein and the decrease on MCL-1 levels, without changes in BCL-2 levels. In CLL cells, BIM is associated with MCL-1, so the decrease in MCL-1 levels would make CLL cells susceptible to this BH3-only protein. BIM, as well truncated Bid, have dual functions as both inhibitors of anti-apoptotic BCL-2 members and direct activators of pro-apoptotic BAX and BAK. In this sense, the increase in BIM levels, together with Bid activation would lead to BAX and BAK activation, and together with MCL-1 decrease, the remaining anti-apoptotic capacity of BCL-2 would be overwhelmed. The results provided herein show that the degree of MCL-1 decrease together with BIM increase exerted by forodesine significantly correlated with apoptosis induction, and MCL-1 and BIM basal levels could determine the sensitivity of CLL cells to forodesine.

Activation of the mitochondrial apoptotic pathway independent of p53 status has been demonstrated. It has been reported that p73 induction, a transcriptional target of p53, is able to overcome the resistance to apoptosis of CLL cells lacking functional p53. In response to several chemotherapeutic drugs, the pro-apoptotic form of p73, TAp73, trans-activates several p53 target genes that control cell cycle arrest and apoptosis in a way dependent but also independent of p53 status. It was found that forodesine induced p53, and also TAp73 in CLL cells with functional p53, but interestingly, p73 mRNA and protein levels also increased in CLL cells with p53 deletion. Oxidative stress and ROS production leads to activation of TAp73, as well E2F1, being both proteins implicated in mitochondrial apoptotic pathway activation through p53-dependent and independent mechanisms. Therefore, the elevation of ROS induced by forodesine could provide a signal that activates E2F-1 and/or up-regulates TAp73. The FOXO family of transcription factors regulate the expression of many genes involved in apoptosis, and can be activated by increased oxidative stress. FOXO1 and FOXO3a are transcripitonal targets of E2F-1 and have been shown to be essential for ROS-induced apoptosis, as well being transcription factors of BIM expression in hematopoietic cells. In addition, upon several apoptotic stimulus, ROS scavengers block the induction of FOXO3a and BIM. It has been described that the expression of both FOXO1 and BIM and subsequent apoptosis is regulated by p73 in tumoral cells defective of p53. After forodesine treatment, a protein and mRNA marked up-regulation of p73 and BIM independent of p53 status was shown, as well an increase in FOXO1 and FOXO3a levels, increased that was detected at early times. The expression of FOXO-regulated target genes can be controlled by any of the FOXO members, suggesting a redundant mechanism of action, as shown by the transcriptional regulation of BIM exerted by both FOXO1A and FOXO3A.

Thus, the results described herein provide evidence of a mechanism involved in forodesine induced cell death in CLL cells independent of p53 status, revealing that different programmed cell death pathways can coexists in the same cell and can be selectively induced by diverse stimuli.

These results indicate that forodesine as a single agent, or in combination with bendamustine or rituximab, to be highly effective in the treatment of CLL. Therefore, forodesine, available, e.g., in oral and intra-venous formulation with low toxicity profiles, is a treatment option for patients with poop prognosis (e.g., 17p-), patients with refractory disease and/or treatment option for elderly patients. A multi-centre, open-label phase I clinical trial of forodesine in relapsed CLL patients has been initiated.

A. Methods of Treating Hematologic Cancers

Provided herein are methods of treating hematologic cancers, for example, cancers of the blood, in a subject. Examples of these types of cancers include, e.g., acute myeloid leukemia, chronic myeloid leukemia, acute lymphoblastic leukemia (ALL), chronic lymphocytic leukemia (CLL), myeloproliferative diseases, multiple myeloma, and myelodysplastic syndrome, Hodgkin's lymphoma, non-Hodgkin's lymphoma (malignant lymphoma) and Waldenstrom's macroglobulinemia. In some embodiments, the hematologic cancer is CLL. In other embodiments, the hematologic cancer is ALL.

A subject can include both mammals and non-mammals. Mammals include, for example, humans; nonhuman primates, e.g. apes and monkeys; cattle; horses; sheep; rats; mice; pigs; and goats. Non mammals include, for example, fish and birds.

In one embodiment, the method includes administering a purine nucleoside phosphorylase (PNP) inhibitor and an alkylating agent or an anti-CD20 agent to the subject. In certain embodiments, a PNP inhibitor and an alkylating agent are administered. In another embodiment, a PNP inhibitor and an anti-CD20 agent are administered. In yet another embodiment, a PNP inhibitor is administered after identifying a subject resistant to one or more chemotherapeutic agents (e.g., Bendamustine or Fluarabine). In a further embodiment, a PNP inhibitor is administered after detecting a p53 deletion in a subject.

Without being bound by theory, a PNP inhibitor can induce an increase of plasma 2'-deoxyguanosine (dGuo) and the accumulation of intracellular deoxyguanosine triphosphate (dGTP) leading to cell death induction. Non-limiting examples of PNP inhibitors can include those disclosed in U.S. Pat. Nos. 4,985,433; 4,985,434, 5,008,265; 5,008,270; 5,565,463 and 5,721,240 assigned to BioCryst Pharmaceuticals, Inc., disclosures of which are incorporated herein by reference. In certain embodiments, the PNP inhibitor is Forodesine or a salt thereof, including the HCl salt:

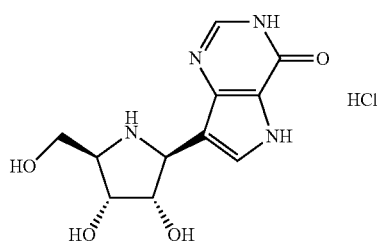 [SMILES: O=c1[nH]cnc2c([C@@H]3N[C@H](CO)[C@@H](O)[C@H]3O)c[nH]c12 ; Cl]

Without being bound by theory, an alkylating agent refers to a chemotherapeutic compound that chemically modifies DNA and disrupts its function. Some alkylating agents cause formation of cross links between nucleotides on the same strand, or the complementary strand, of a double-stranded DNA molecule, while still others cause base-pair mismatching between DNA strands. An alkylating agent can be a mustard derivative, a nitrosourea derivative, a platinum compound, or an imidazole carboxamide compound. Examples of alkylating agents include Bendamustine, Busulfan, Carboplatin, Carmustine, Cisplatin, Chlorambucil, Cyclophosphamide, Dacarbazine, Hexamethylmelamine, Ifosphamide, Lomustine, Mechlorethamine, Melphalan, Mitotane, Mytomycin, Pipobroman, Procarbazine, Streptozocin, Thiotepa, and Triethylenemelamine. In some cases, the alkylating agent can be Bendamustine, or a salt thereof, including the HCl salt:

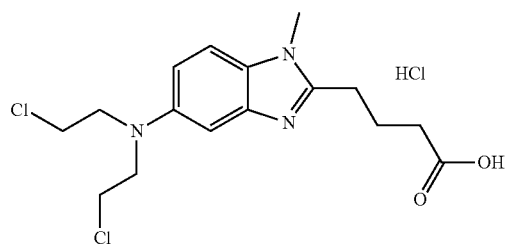 [SMILES: Cn1c(CCCC(=O)O)nc2cc(N(CCCl)CCCl)ccc21 ; Cl]

An anti-CD20 agent can be any agent that targets (e.g., selectively binds to) the B-cell cells surface protein CD20. In some embodiments, the anti-CD20 agent is an antibody specific for CD20. Without being bound by theory, it is thought that these agents can operate by one of three mechanisms: (1) complement-mediated cytotoxicity; (2) antibody-dependent cell-mediated cytotoxicity; and (3) induction of apoptosis. Examples of anti-CD20 agents include Rituximab, Ibritumomab, Trastuzumab, Gemtuzumab, and Alemtuzumab. In some embodiments, the anti-CD20 agent is Rituximab.

The PNP inhibitor, alkylating agent, and/or anti-CD20 agent can be administered by any route, e.g., intra-operative, intrathecal, intradiskal, peridiskal, epidural (including periradicular and transforaminal), any combination of intradiskal, epidural, and peridural, perispinal, IV, intramuscular, SC, oral, intranasal, inhalation, transdermal, and parenteral.

The PNP inhibitor, alkylating agent, and/or anti-CD20 agent can be formulated with a pharmaceutically acceptable carrier selected on the basis of the selected route of administration and standard pharmaceutical practice. The PNP inhibitor, alkylating agent, and/or anti-CD20 agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the PNP inhibitor, alkylating agent, and/or anti-CD20 agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the PNP inhibitor, alkylating agent, and/or anti-CD20 agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the PNP inhibitor, alkylating agent, and/or anti-CD20 agent may be combined with one or more solid inactive ingredients for the preparation of tablets, capsules, pills, powders, granules or other suitable oral age forms. For example, the PNP inhibitor, alkylating agent, and/or anti-CD20 agent may be combined with at least one excipient such as fillers, binders, humectants, disintegrating agents, solution retarders, absorption accelerators, wetting agents absorbents or lubricating agents.

The specific dose of a PNP inhibitor, alkylating agent, and/or anti-CD20 agent will, of course, be determined by the particular circumstances of the individual patient including the size, weight, age and sex of the patient, the nature and stage of the disease being treated, the aggressiveness of the disease disorder, and the route of administration of the compound. Doses and schedules of the compounds, e.g., forodesine, bendamustine and rituximab, may be administered singly or in combination according to, e.g., doses and schedules indicated in FDA approved labels.

In some embodiments, the PNP inhibitor and alkylating agent or anti-CD20 agent are administered concurrently, while in other embodiments the PNP inhibitor and alkylating agent or anti-CD20 agent are administered sequentially. In one embodiment, the alkylating agent or anti-CD20 agent can be administered one or more times prior to administration of the PNP inhibitor (e.g., two times, three times, four times, five times, 10 times, or 20 times). In a further embodiment, the PNP inhibitor may be administered one or more times prior to the administration of the alkylating agent or anti-CD20 agent (e.g., two times, three times, four times, five times, 10 times, or 20 times).

In some embodiments, treatment of a hematologic cancer in a subject may include identifying a subject who is resistant to one or more chemotherapeutic agents. One of the main causes of failure in the treatment of cancer is the development of drug resistance by the cancer cells. This is a very serious problem that may lead to recurrence of disease or even death. In one embodiment, the subject resistant to one or more chemotherapeutic agents can be identified by means known in the art. The subject may be resistant to any known chemotherapeutic agent. In certain embodiments, the subject can be resistant to an alkylating agent (e.g., Bendamustine) and/or purine nucleoside analogue (e.g., Fluradadine).

Following identification of a chemotherapeutic resistant subject, the subject can be administered a PNP inhibitor. In some embodiments, the PNP inhibitor is Forodesine HCl.

In another embodiment, treatment of a hematologic cancer in a subject can include the detection of the presence of a p53 deletion, e.g. a 17p deletion, in one or more cancer cells in a sample from the subject. The 17p deletion is a marker that can identify a hematologic cancer subject that may exhibit a different biological and clinical behavior. For example, p53 alterations can convey drug resistance and shorter survival periods.

In one embodiment, a subject that presents a p53 deletion can be administered a PNP inhibitor. In select embodiments, the PNP inhibitor is Forodesine HCl.

The methods of treatment discussed above involve both monotherapy and combination therapy. In the context of combination therapy, the disclosure envisions the administration of two or more chemotherapeutic agents, in particular, a PNP inhibitor and an alkylating agent or a PNP inhibitor and an anti-CD20 agent. Some of these compounds have already been approved for use in treating one or more cancer indications. Others are in various stages of pre-clinical and clinical development.

In some embodiments, administration of a PNP inhibitor and an alkylating agent or anti-CD20 agent can produce a synergistic effect. This effect can be demonstrated through the development of a combination index (CI). In certain embodiments, the index can be calculated as a function of the fraction of cells affected according to the procedure of Chou et al., *Advance Enz. Regul.*, 22, 27-55 (1985). This is a well-known test that evaluates coefficient interactions against a range of cell death proportions. For example, if treatment with drug A results in 30% cell death and treatment with drug B results in 50% cell death, than it would be expected that the combination of the two drugs would result in 65% cell death. Accordingly, if the ratio of the predicted cell death to that actually measured upon combination of the drugs is less than one, then a synergistic effect is observed. If, however, the ratio is greater than one, then an antagonistic effect is observed. In one embodiment, the combination of Forodesine and Bendamustine shows a synergistic effect, while the combination of Forodesine and Fludarabine shows an antagonistic effect (see Example 5).

B. Pharmaceutical Compositions

Provided herein are pharmaceutical compositions comprising a PNP-inhibitor and an alkylating agent or a PNP-inhibitor and an anti-CD20 agent. In some embodiments, a PNP-inhibitor can include Forodesine (BCX-1777). In certain embodiments, an alkylating agent can include Bendamustine. In other embodiments, an anti-CD20 agent is Rituximab.

The pharmaceutical compositions provided herein contain a PNP inhibitor and an alkylating agent or a PNP-inhibitor and an anti-CD20 agent in amounts that are useful in the treatment of hematologic cancers, and a pharmaceutically acceptable carrier. Pharmaceutical carriers suitable for administration of the compounds provided herein include any such carriers known to those skilled in the art to be suitable for the particular mode of administration.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of the PNP inhibitor and the alkylating agent or a PNP-inhibitor and an anti-CD20 agent in the pharmaceutical composition will depend on absorption, inactivation and excretion rates of the compounds, the physicochemical characteristics of the compounds, the dosage schedule, and amount administered as well as other factors known to those of skill in the art. For example, the amount that is delivered is sufficient to treat chronic lymphocyte leukemia, as described herein.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing a PNP inhibitor and an alkylating agent or a PNP-inhibitor and an anti-CD20 agent in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

C. Kits

Also provided herein are kits. Typically, a kit includes a PNP inhibitor and an alkylating agent or a PNP-inhibitor and an anti-CD20 agent. In certain embodiments, a kit can include one or more delivery systems, e.g., for the PNP inhibitor, the alkylating agent, the anti-CD20, or any combination thereof, and directions for use of the kit (e.g., instructions for treating a subject). In certain embodiments, a kit can include the PNP inhibitor and/or the alkylating agent. In another embodiment, a kit can include the PNP inhibitor and/or the anti-CD20 agent. In some embodiments, the kit can include a PNP inhibitor and a label that indicates that the contents are to be administered to a subject resistant to alkylating agents, such as Bendamustine. In another embodiment, the kit can include a PNP inhibitor and a label that indicates that the contents are to be administered to a subject with a p53 deletion (e.g., a 17p deletion). In a further embodiment, a kit can include a PNP inhibitor and a label that indicates that the contents are to be administered with an alkylating agent or an anti-CD20 agent.

D. Definitions

As used herein, the singular forms "a," "an," and "the" include plural referents unless the context clearly dictates otherwise.

The expression "effective amount", when used to describe an amount of compound in a method, refers to the amount of a compound that achieves the desired pharmacological effect or other effect, for example an amount that inhibits the abnormal growth or proliferation, or induces apoptosis of cancer cells, resulting in a useful effect.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

EXAMPLES

Example 1: Forodesine Cytotoxicity in CLL-ZAP-70$^{high}$ Versus ZAP-70$^{Low}$

Figure 1B:
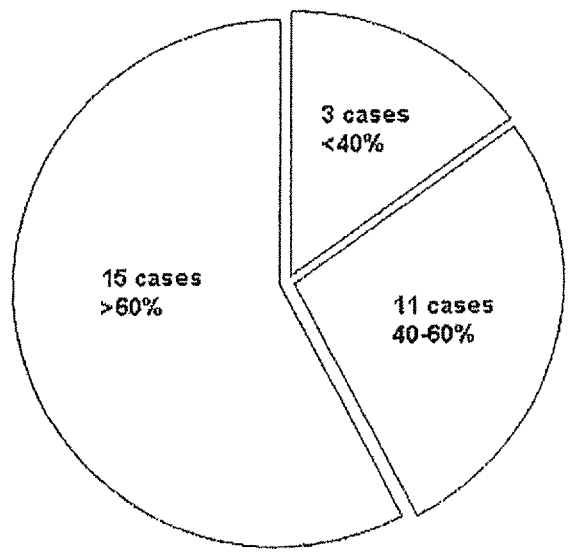

Cells from 16 CLL patients with high ZAP-70 levels (>20%) and from 13 CLL patients with low ZAP-70 levels (<20%) were treated with Forodesine 2 µM+dGuo 20 µM for 48 hours. Cytotoxicity was analyzed by Annexin V-FITC staining (expressed as percentage of control, untreated cells). Results indicated that the mean cytotoxicity for both high and low ZAP-70 levels was greater than 50% (see FIGS. 1A and 1B).

Example 2: Intracellular Increase in dGTP Levels

Figure 2:
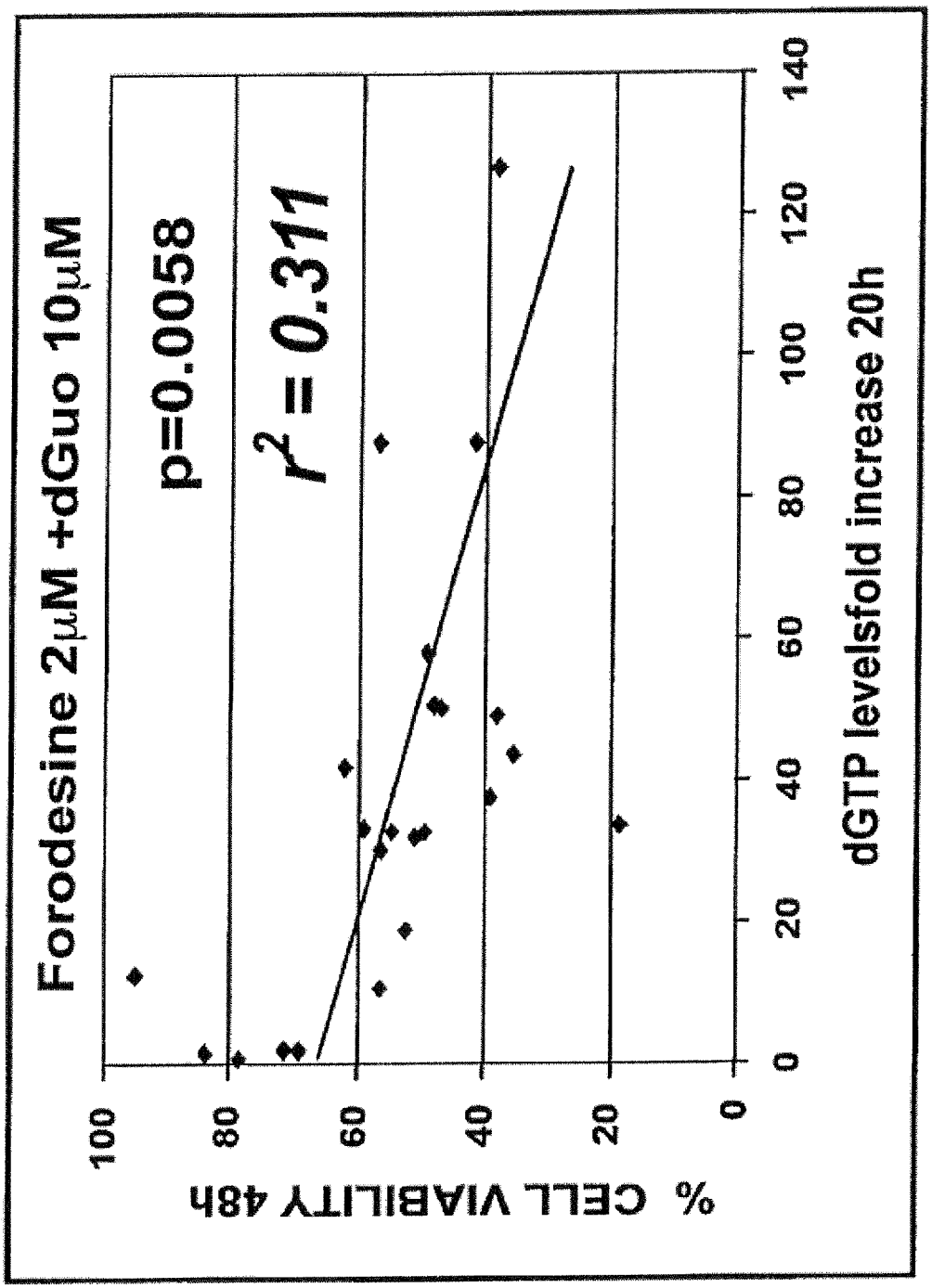
FIG. 2 displays the correlation between an intracellular increase in dGTP levels after Forodesine treatment and amount of cell death induced.

Cells from 26 CLL patients were treated with Forodesine for 20 hours. Total nucleotides were extracted (60% methanol) and dGTP levels were quantified by DNA polymerase assay. Cell viability compared to control (untreated cells) was analyzed at 48 hours by Annexin V-FITC staining. The intracellular increase in dGTP levels after Forodesine treatment correlates well with the cell death induced (see FIG. 2).

Example 3: Response of p53 Deleted CLL Cases to Forodesine

Cells from 11 CLL patients with 17p deletions (g=>85% of cells, FISH analysis) were treated with Forodesine 2 µM+dGuo 20 µM, Bendamustine 25 µM or Fludarabine 1 µg/mL for 48 hours. Results indicated that p53 deleted CLL cases showed high response to Forodesine (see FIG. 3).

Example 4: Effect of Forodesine on CLL Cases with Chemotherapeutic Resistance

Figure 4:
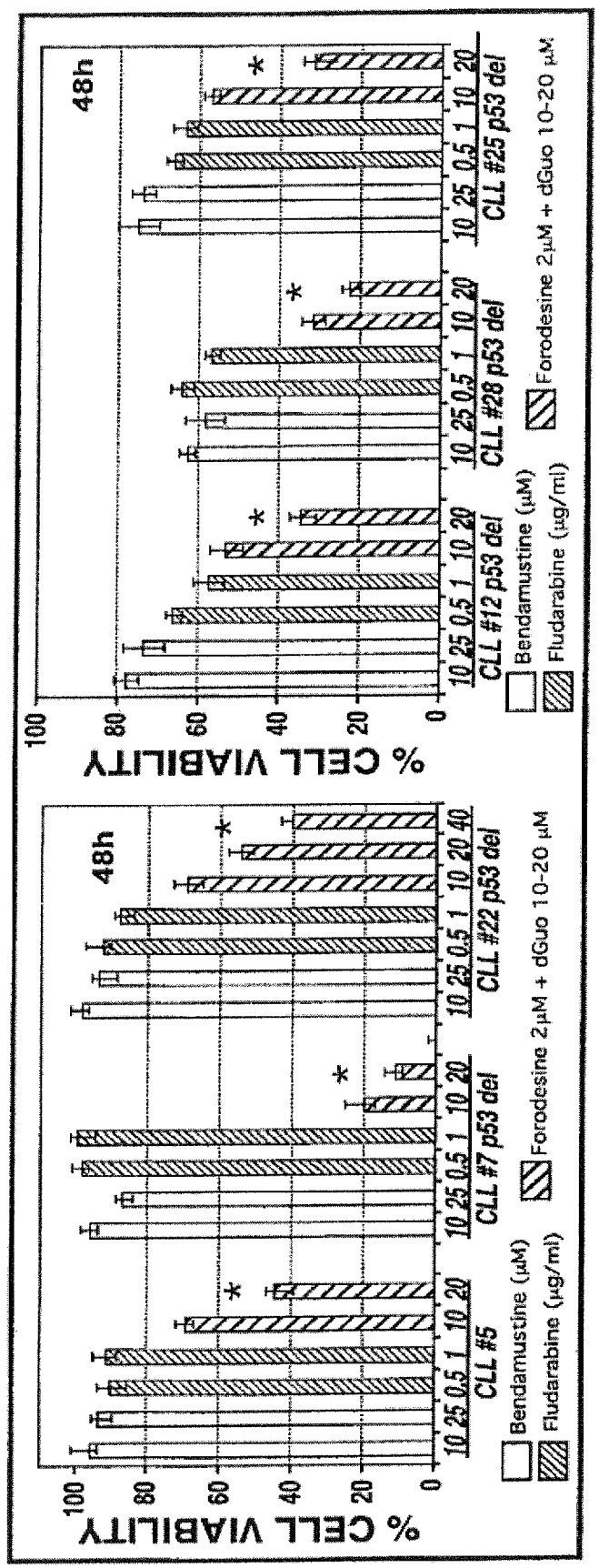
FIG. 4 displays the data for treatment with Forodesine of CLL cases with low or no sensitivity to Bendamustine or Fludarabine treatment.

Cells from CLL patients that were found to have low or no sensitivity to Bendamustine or Fludarabine were treated with Forodesine 2 µM and dGuo 10-20 µM. Results indicated that these cells showed a good response to Forodesine treatment (see FIG. 4).

Figure 5B:
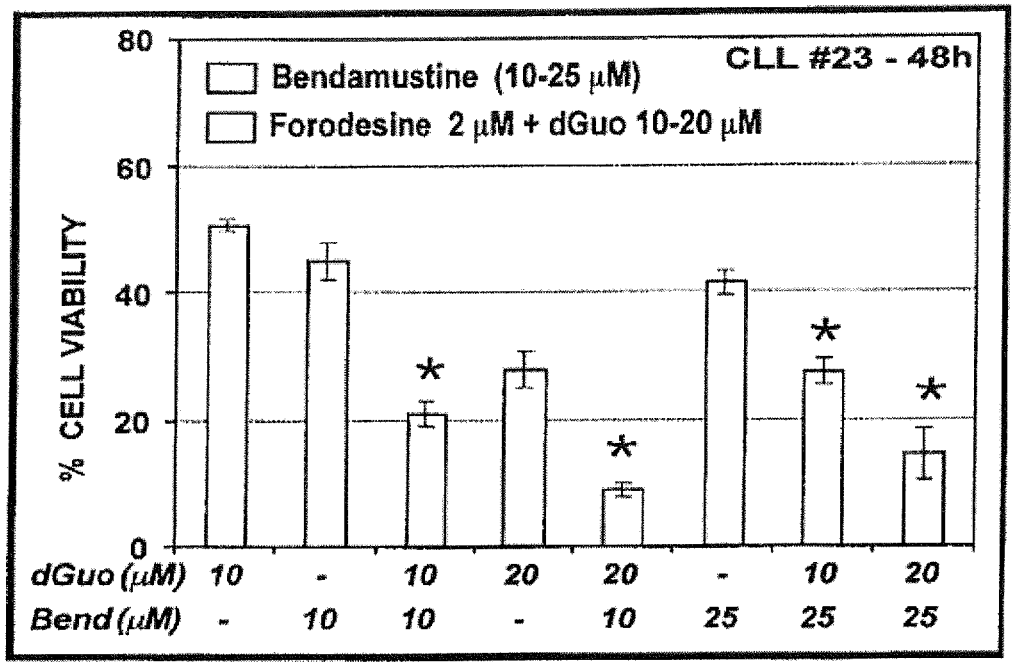

Example 5: Effect of Forodesine/Bendamustine and Forodesine/Fludarabine Combinations Cells from CLL patients were treated with Forodesine 2 µM+dGuo 10-20 µM and Bendamustine 10-25 µM or Fludarabine 3.75-7.5 µM for 48 hours. The combination index (CI) was analyzed after 48 hours. A CI value less than 1 is indicative of a synergistic effect (Chour & Talalay's algorithm), while a CI value greater than 1 is indicative of an antagonistic effect. Results indicated that Forodesine/Bendamustine have a synergistic effect, while Forodesine/Fludarabine have an antagonistic effect (see FIGS. 5A and 5B).

Example 6: Effect of Forodesine/Rituximab Combination

Cells from 7 CLL patients (3 with high levels of ZAP-70 (>35%) and 4 with p53 deletions) were treated with Forodesine HCl 2 µM+dGuo 10-20 µM and Rituximab 25-50 µM for 24-48 hours. The combination index (CI) was analyzed after 48 hours. The cells were analyzed by flow cytometry using Annexin V-FITC staining and PI permeability assays. A CI value less than 1 is indicative of a synergistic effect (Chour & Talalay's algorithm), while a CI value greater than 1 is indicative of an antagonistic effect. Results indicated that the Forodesine/Rituximab combination has a synergistic effect (see FIG. 6).

Example 7: Forodesine Induces p53-Independent Mitochondrial Apoptosis

As described herein, the purine nucleoside phosphorylase inhibitor forodesine induces p53-independent mitochondrial apoptosis in chronic lymphocytic leukemia cells through Mcl-1 downregulation and induction of p73 and Bim.

Chronic lymphocytic leukemia (CLL) is a clinical heterogeneous entity derived from the monoclonal expansion of long-life CD5+ B-lymphocytes with abnormal regulation of apoptosis and low proliferation rates. In spite of recent advances, the new therapies in the treatment of CLL have not improved the overall survival of the patients and many patients eventually developed drug resistance. An unmutated profile of immunoglobulin genes, high expression of ZAP-70 protein, high CD38 expression and the presence of certain cytogenetic abnormalities (especially deletions of 17p13 (TP53) and 11q22-q23 (ATM)) are associated with poorer overall survival and a shorter time to disease progression of CLL patients. Chemotherapeutic anti-cancer drugs induce apoptosis usually either via DNA damage response and p53 activation, and/or directly via perturbation of mitochondrial function. The DNA-damage response pathway appears to play a key role in CLL drug-induced apoptosis, as cells from CLL patients with TP53 abnormalities show resistance to conventional chemotherapy and short survival. The lack of p53 function by deletion of p53 and mutation of the remaining allele increases in CLL patient's refractory to chemotherapy, being "double-hits" during the acquisition of drug resistance that abrogates the transcriptional and mitochondrial apoptotic activity of p53. Therefore, new effective approaches should induce apoptosis through DNA-damage-independent pathways and/or direct activation of apoptotic pathways independent of p53.

A hallmark of CLL cells is their resistance to apoptosis induction, being Bcl-2 family proteins critical regulators of apoptosis and survival in CLL cells. High levels of anti-apoptotic Bcl-2 and Mcl-1 proteins are associated with aggressive disease and resistance to chemotherapy in CLL. MCL-1 has also an important role in prolonging the CLL cell survival, as MCL-1 levels inversely correlated with in vitro and clinical response to several drugs.

Purine nucleoside phosphorylase (PNP) is an enzyme in the purine salvage pathway that phosphorylates purine analogues to their respective bases and deoxyribose phosphate. Forodesine or immucillin H (BCX-1777) is a potent transition-state analogue inhibitor of PNP that has demonstrated inhibition of T-cell proliferation in vitro and in vivo Bantia et al., *Int Immunopharmacol*, 1(6), 1199-210 (2001); Kicska et al., *PNAS*, 98(8), 4593-4598 (2001); Bantia et al., *Int Immunopharmacol*, 3(6), 879-887 (2003); and Gandhi et al., *Semin Oncol*, 34(6 Suppl 5), S8-12 (2007)). Forodesine has shown a low toxicity profile (Gandhi et al., *Blood*, 106(13), 4253-4260 (2005); and Korycka et al., *Mini Rev Med Chem*, 7(9), 976-983 (2007)) and is being studied in clinical trials for patients with T-cell prolymphocytic leukemia, cutaneous T-cell lymphoma and B-cell acute lymphoblastic leukemia (Galmarini et al., *IDrugs*, 9(10), 712-722 (2006)). Also, forodesine appears to exert an ex vivo cytotoxic effect in CLL cells (Balakrishnan et al., *Blood*, 108(7), 2392-2398 (2006)). PNP inhibition results in elevation of plasma 2' deoxyguanosine (dGuo) levels and subsequent intracellular accumulation of deoxyguanosine triphosphate (dGTP) in those cells with high levels of deoxynucleoside kinase activity, leading to apoptosis induction in T-lymphocytes. CLL cells have high (dCK) activity, which is a primary enzyme for the conversion of dGuo to dGMP, which is then converted to dGTP, being CLL cells susceptible to PNP inhibition. Unlike others purine nucleoside analogs, such as fludarabine or bendamustine, forodesine is not incorporated into DNA and represents a new class of selective anti-tumour agent with a novel and not fully understood mechanism of action.

As described herein, the cytotoxic effect of forodesine in primary leukemic cells from 43 patients with CLL, as well the evaluation of the in vitro combination of forodesine with drugs used in the clinical practice, such as fludarabine, bendamustine and rituximab, were evaluated. Based on these results, forodesine appears to be a highly effective therapy in the treatment of CLL patients independent of their ZAP-70, CD38, p53 status or cytogenetic abnormalities. Further, forodesine appears to induce activation of the mitochondrial apoptotic pathway by decreasing the levels of Mcl-1 protein and induction of p73 and pro-apoptotic Bim protein. Interestingly, no significative differences in these apoptotic markers were observed based on p53 status, suggesting a common apoptotic pathway independent of p53-mediated cell death.

Forodesine Induced Apoptosis in Primary Cells from CLL Patients Independent of ZAP-70, CD38 and Cytogenetic Status.

A dose escalation study was conducted to evaluate the in vitro forodesine cytotoxicity in primary leukemic lymphocytes from CLL patients. In order to obtain an in vitro cytotoxic effect, an external source of dGuo was added together with forodesine. Incubation of CLL cells with pharmacologically achievable levels of forodesine (2-5-10 $\mu$M) with increasing doses of dGuo (10-20 or 30 $\mu$M) for 48 hours induced cell death (analyzed by Annexin-V+ staining), whereas forodesine or dGuo alone did not induce a cytotoxic effect. No differences on cell death were observed using higher doses of forodesine (even up to 15 $\mu$M). On the contrary, increasing the dose of dGuo resulted in a higher induction of cell death, so the subsequent studies were performed using a single dose of forodesine (2 $\mu$M) together with 10 or 20 $\mu$M of dGuo.

Next, the cytotoxic effect of forodesine and dGuo were analyzed in primary leukemic cells from 43 patients with CLL. A mean cytotoxicity with respect to control of 44.2%±11.4 and 57.4%±13.1 at 24h and 48 h respectively was observed. The cytotoxic effect was higher than 60% in 21 cases (48.8% of total), between 40-60% in 18 cases (41.8% of total) and lower than 40% in only 4 cases (9.4% of total). No differences on cell death were observed between the use of cryopreserved primary CLL samples (n=32, 58.3%±11 at 48 hours) and CLL fresh samples (n=10, 56.6%±6.4 at 48 hours). Cytotoxicity of forodesine 2 $\mu$M and dGuo (10-20 $\mu$M) in PBMCs from healthy donors was relatively lower compared to CLL cells, both in T-lymphocytes (CD3$^+$ cells) and B-lymphocytes (CD19$^+$ cells).

In CLL patients, the expression levels of ZAP-70 and/or CD38 proteins are associated with poorer overall survival and a shorter time to disease progression (Hus et al., *Ann Oncol*, 17(4), 683-690 (2006)). Significant differences were not observed between the cell death induced by forodesine in those CLL cells with low levels of ZAP-70 (17 CLL patients; 58.1%±11 of mean cytotoxicity with respect to control) and those CLL cells which express high levels of ZAP-70 (22 CLL patients; 57.9%±12 of mean cytotoxicity), as well regarding the CD38 expression levels (CD38 low 52.3%±12 vs. CD38 high 62.1%±12 of mean cytotoxicity). Furthermore, the most common cytogenetic alterations in CLL cells, such as 13q deletion, 11q deletion and 17p deletion associated with in vitro and in vivo drug resistance and short survival of CLL patients, did not correlate with forodesine-induced cytotoxicity, with a good response also achieved in these cases.

The cytotoxic response of CLL cells treated with forodesine versus fludarabine or bendamustine cytotoxicities, two main chemotherapeutic agents used in CLL (Aivado et al., *Semin Oncol*, 29, (4 Suppl 13), 19-22 (2002); and Montserrat, *Hematol J*, 5, Suppl 1, S2-S9 (2004)), were also compared. Primary CLL cells from 32 CLL patients, 11 of them with p53 deletions, were incubated with forodesine 2 $\mu$M and dGuo 20 $\mu$M, bendamustine 10-25 $\mu$M and fludarabine 1 $\mu$g/mL for 48 hours alone or in combination. As single agents the mean cytotoxicity in CLL with no 17p deletion was 55.3±8, 50.6±11 and 49.2±18 for forodesine, fludarabine and bendamustine, respectively. The acquisition of 17p deletion, leading to p53 alterations, is associated with in vitro and in vivo fludarabine resistance in CLL patients (Dohner et al., *Blood*, 85(6), 1580-1589 (1995); and Turgut et al., *Leuk Lymphoma*, 48(2), 311-320 (2007)). Remarkably, the majority CLL patients with 17p deletion showed a high response to forodesine, with a mean cytotoxicity at 48 hours of 60.1%±21 (forodesine 2 $\mu$M and dGuo 20 $\mu$M). In contrast, these cases showed a lower response to fludarabine (25.1±13 of mean cytotoxicity) and bendamustine (36.2%±17 of mean cytotoxicity). In addition, in 12 of 32 CLL patient samples analyzed, no or low in vitro response (cytotoxicity lower than 35% with respect to control) to bendamustine 25 $\mu$M and/or fludarabine 1 $\mu$g/ml were observed, but they showed a high response to forodesine. Three cases with 17p deletion with low or very low response to bendamustine or fludarabine showed a high response to forodesine (67%±20 of mean cytotoxicity) and only two CLL patients showed a low response to forodesine.

Combinations of Forodesine with Fludarabine, Bendamustine and Rituximab.

The combination of fludarabine with forodesine for treatment was evaluated. The combination of forodesine with bendamustine, an alkylating agent and also a purine-like analogue, was also evaluated. Combinations of forodesine 2 $\mu$M and dGuo (10-20 uM) with fludarabine (0.5-1 $\mu$g/ml) did not increase the cytotoxic effect of either drug as a single agent, and a negative effect on cell death induction was observed. In order to evaluate the combination effect between both drugs, the combination index or CI value was calculated using Chou and Talalay's algorithm (Chou et al., *Adv Enzyme Regul*, 22, 27-55 (1984)) as an indicative marker for the antagonic or synergistic effect for the combination of two different drugs. Briefly, a CI value higher than 1 is indicative of an antagonistic effect, whereas a CI value lower than 1 is indicative of a synergistic effect. The combination studies performed with fludarabine and forodesine showed CI values higher than 1 in all CLL cases analyzed (48 hours), indicating an antagonic effect between both drugs. The mean cytotoxicity achieved with the forodesine and fludarabine combination was lower than caused by both drugs. Forodesine was also effective in those CLL cases with low response to bendamustine, but in contrast to fludarabine, a high increase on cell death was observed with the combination of bendamustine and forodesine and a potent synergistic effect (CI<1) was observed. Frodesine clearly enhance the cytotoxic response of a low dose of bendamustine (10 $\mu$M, mean cytotoxicity of 32.95%), achieving a mean cytotoxic effect for the combination of both drugs of 70.5%.

The combination of forodesine and rituximab, a humanized monoclonal antibody against CD20, was also evaluated. At 24 hours, the cell death observed with rituximab (25-50 11 g/flap as a single agent was low, and the combination with forodesine clearly improved the cytotoxic effect of both drugs. A potent synergistic effect between rituximab and forodesine was also demonstrated, with CI values close to 0.5.

Correlation of Increase in Intracellular dGTP Levels and dCK Phosphorylation at Ser-74 with Forodesine Induced Cell Death.

The intracellular levels of dGTP in primary cells from 26 CLL patients treated with forodesine 2 µM and dGuo 10 µM was analyzed. A significant direct correlation (p<0.05) between the fold increase in the dGTP levels analyzed at 18 hours and forodesine-cytotoxicity at 48 hours was observed. Forodesine induced a high increase in intracellular dGTP levels (up to 96 times fold increase with respect to control basal levels, reaching values between 6 and 129 pmoles of dGTP/$10^6$ millions of cells). Four CLL cases showed no or low increase in dGTP levels, and a low cytotoxic response to forodesine was observed in these cases. To confirm that the increase on dGTP levels after forodesine treatment was mediated by the phosphorylation of dGuo by dCK, the cell death induction in the presence of deoxycytidine was analyzed. As deoxycytidine is the primary substrate of dCK, it should inhibit the phosphorylation of dGuo by dCK, affecting the intracellular increase in dGTP and subsequent apoptosis induced by forodesine. Pre-incubation of cells with deoxycytidine (5-10 µM) inhibited forodesine-induced cell death. Some nucleoside analogues used in anti-cancer chemotherapy, in particular, the purine analogue fludarabine and the deoxycytidine analogue gemcitabine, are phosphorylated by dCK in order to be active. Deoxycytidine also reverted the loss of cell viability induced by fludarabine, whereas cell death induced by bendamustine (drug that may acts independent of dCK) was not reverted.

The phosphorylation status of dCK was analyzed by western blot upon forodesine treatment, as it has been recently described that in CLL cells dCK activity is positively regulated by phosphorylation at Ser-74 (Smal et al., *J Biol Chem,* 281(8), 4887-4893 (2006); Smal et al., *Nucleosides Nucleotides Nucleic Acids,* 25(9-11), 1141-1146 (2006); Smal et al., *Cancer Lett,* 253(1), 68-73 (2007)). An increase in the phosphorylated form (at Ser-74) of dCK in CLL cells was observed, an increase not exerted by bendamustine. Densitometric analysis of phosho-dCK/dCK ratio after forodesine treatment was performed, and a correlation with cytotoxicity was observed, both at 24 (p=0.05, supplemental data) and 48 hours (p=0.05).

In order to investigate the antagonic effect observed between fludarabine and forodesine, the intracellular dGTP increase after incubation of CLL cells with fludarabine (1 µg/ml) and forodesine (2 µM and dGuo 10 µM) was observed. Fludarabine alone did not induce an increase in dGTP levels, whereas the combination of fludarabine with forodesine (grey bars) reduced the dGTP fold increase exerted by forodesine alone (black bars). Therefore, the reduction of dGTP increase observed with the fludarabine and forodesine combination would explain the antagonic effect observed between both drugs. As fludarabine needs to be phosphorylated by dCK to be active, and dGuo is also phosphorylated by this enzyme, both drugs might be competing for the same enzyme, and therefore the formation of dGTP or the active form of fludarabine would be reduced.

Forodesine Induced Activation of the Mitochondrial Apoptotic Pathway Independent of p53.

To elucidate the mechanism of action by which forodesine induced apoptosis in CLL cells, several hallmarks of mitochondrial apoptotic pathway were analyzed. Forodesine induced loss of mitochondrial transmembrane potential ($\Delta\psi m$) at early times. Reactive-oxygen species (ROS) can be generated after mitochondrial damage and may subsequently mediate apoptosis (Villamor et al., *Curr Pharm Des,* 10(8), 841-853 (2004)). Forodesine also induced the production of ROS in CLL primary cells. Mitochondrial depolarization and ROS production was observed as early events, as they were evident after 10 hours of treatment with forodesine. Oxidative stress plays a role in regulating programmed cell death, so the effect of several ROS scavengers was analyzed. Pre-incubation of CLL cells with glutathione-reduced ethyl ester (GSH), N-acetyl cysteine (NAC) or Tiron reduced $\Delta\psi m$ loss and ROS production induced by forodesine. NAC and Tiron (specific scavengers of $O_2$) practically reverted ROS production, whereas the effect of GSH, a scavenger selective for $H_2O_2$, was moderated.

A previous in vitro study in CLL cells reported that forodesine results in p53 stabilization and apoptosis induction (Balakrishnan et al., *Blood,* 108(7), 2392-2398 (2006)), results that are consistent with other anticancer drugs that induce DNA damage and p53-mediated apoptosis. But, unlike others purine nucleoside analogs, forodesine is not incorporated into DNA. Interestingly, the early hallmarks of the mitochondrial apoptotic pathway analyzed were also observed in CLL patients with 17p (p53) deletion or 11q (ATM) deletion, indicating a mechanism of apoptosis initiation independent of DNA damage p53-mediated response.

Forodesine Triggered Sequential Caspase-9 and -8 Activation and Processing of BID, Suggesting the Role of an Amplification Loop of the Mitochondrial Apoptotic Pathway Mediated by Caspase-8.

In order to investigate the downstream signaling pathways that lead to mitochondrial apoptosis, the pattern of caspase activation after forodesine exposure was investigated. A dose- and time-dependent activation of caspase-9, -8 and -3 was observed and analyzed by the processing of their pro-inactive form. The cleavage products of pro-caspase-9 and -8 were present almost simultaneously as early as 10 hours of forodesine treatment, being the p37 cleaved form of pro-caspase-9 first, followed by the increase in the p43/41 cleaved form of caspase-8. The cleavage of pro-caspase-3 and the presence of its active form was detected later. In correlation with activation of caspase-8, forodesine also induced a decreased of BH3-only protein BID, a main substrate of caspase-8, to give its truncated pro-apoptotic form, that also activates the mitochondrial apoptotic pathway. A decrease of the inhibitors of apoptosis XIAP and survivin and the proteolityic cleavage of PARP, a caspase-3 substrate was also observed, in correlation with apoptosis induction. Next, the role of caspase activation in forodesine-induced apoptosis was investigated, as activation of the mitochondrial apoptotic pathway leads to caspase-dependent but also independent cell death. Treatment of cells with the broad range caspase inhibitor z-VAD.fmk partially reduced phospatidylserine exposure after forodesine treatment for 24 hours, suggesting the implication of both, caspase-dependent as well independent mechanisms of action.

Activation of caspase-8/BID might play a key role during apoptosis induction exerted by forodesine, or be a secondary side-event due to caspase-9 activation and therefore downstream of mitochondria. Interestingly, apoptosis induction, analyzed by Annexin V staining, was partially blocked by the specific caspase-8 inhibitor z-IETD.fmk, whereas the reversion on $\Delta\Psi m$ loss observed was more pronounced. Collectively, these results suggest that caspase-8 activation and BID plays an early amplification role during the mitochondrial apoptotic pathway induced by forodesine.

Analysis of Pro-Apoptotic and Anti-Apoptotic Regulators of the Mitochondria Mediated Cell Death.

The mitochondrial apoptotic pathway is regulated by a tight balance between pro- and anti-apoptotic members that belong to the BCL-2 family proteins, such as anti-apoptotic BCL-2 and MCL-1 proteins and pro-apoptotic BAX, BAK, BID and BIM proteins among others. CLL cells express high levels of the anti-apoptotic proteins MCL-1 and BCL-2 that inversely correlates with in vitro and clinical response to chemotherapy. The effect of forodesine incubation on the levels of these anti-apoptotic proteins was investigated. Upon forodesine treatment, the levels of the anti-apoptotic MCL-1 protein considerably decreased, whereas BCL-2 protein levels were not affected. The BH3-only protein BIM interacts with BCL-2 and others anti-apoptotic BCL-2 family members to induce apoptosis. Forodesine induced an increase in the protein levels of the pro-apoptotic BIM protein levels. The changes in BIM and MCL-1 protein levels was confirmed by densitometric analysis in seven CLL cases treated with forodesine. A direct correlation was observed between the increase in pro-apoptotic BIM EL protein levels or decrease in MCL-1 levels and cytotoxic response to forodesine, being significate for the MCL-1 decrease ($p=0.04$). In addition, a significant correlation ($p=0.04$) was found when we plotted the ratio (with respect to control) between the decrease in MCL-1 and BIM EL induction against the cytotoxicity observed after forodesine treatment.

BCL-2 and MCL-1 act as guardians of the mitochondrial membrane, preserving its integrity from the action of effector pro-apoptotic proteins, such as BAX and BAK. BIM and truncated BID are the only BH3-only proteins that have the capacity to act as direct activators of BAX and BAK, and the activation of BAX and BAK by flow cytometry after incubation of CLL cells with forodesine was analyzed. Forodesine induced the conformational change of BAX and BAK that allow these proteins to insert into the outer mitochondrial membrane, its oligomerization, the subsequent induction of mitochondrial membrane permeabilization and activation of the cell death machinery.

Forodesine Treatment Triggered an Increase of p73 at mRNA and Protein Levels and the Induction of FOXO1 and FOXO3A.

Although forodesine exerted a cytotoxic effect in all CLL cases irrespective of the p53 status, forodesine was able to induce stabilization of p53 protein in CLL cases with no 17p deletion. Induction of the TAp73 protein, a p53 related protein needed for p53-mediated apoptosis, is able to overcome the resistance to apoptosis of CLL cells lacking functional p53 (Dicker et al., *Blood*, 108(10), 3450-3457 (2006)). Forodesine treatment induces a clear up-regulation of p73 mRNA and TAp73 protein levels in all CLL cases analyzed. p73 regulates the induction of the pro-apoptotic protein BIM through upregulation of the transcription factors FOXO1 and FOXO3a in a way p53-dependent but also p53-independent in tumoral cells (Amin et al., *Cancer Res*, 67(12), 5617-5621 (2007)), although the mechanism of FOXO induction is unknown. The levels of FOXO1 and FOXO3a in CLL cells treated with forodesine was investigated. Forodesine induced an increase in both, FOXO1 and FOXO3a, in correlation with the increase in p73 and BIM protein levels observed.

Materials and Methods
Drugs and Chemicals

Forodesine (BCX-1777/immucillin H) for laboratory use was provided by BioCryst Pharmaceuticals Inc. (Birmingham, USA) and deoxyguanosine (dGuo) was purchased from Sigma. For quantitation of deoxyguanosine triphosphate (dGTP), dNTPs and [$^3$H]dATP were obtained from Amersham Biosciences. Fludarabine (Shering, Berlin, Germany), bendamustine hydrochloride (Treanda™, provided by Cephalon, Inc., Frazer, Pa.), rituximab (Roche, Basel, Switzerland) and 2'-deoxycytidine (Sigma) were used for cytotoxicity assays.

Isolation and Culture of CLL Primary Cells and Peripheral Blood Mononuclear Cells from Healthy Donors The present in vitro study was carried out in primary leukemic lymphocytes from 43 patients diagnosed with CLL according to the World Health Organization classification. Informed consent was obtained from each patient.

Peripheral blood mononuclear cells (PBMCs) cells were isolated by Ficoll/Hypaque sedimentation (Seromed, Berlin, Germany). Cells were either used directly or cryopreserved in liquid nitrogen in the presence of 10% dimethyl sulfoxide and 90% heat-inactivated fetal bovine serum (FBS, Gibco Paisley, Scotland, UK). After thawing, mononuclear cells from CLL patients ($2\times10^6$ cells/mL) were cultured in RPMI 1640 culture medium (Gibco), supplemented with 10% FBS, 2 mM glutamine and 50 µg/mL penicillin-streptomycin, in a humidified atmosphere at 37° C. containing 5% carbon dioxide. The percentage of tumoral cells ($CD19^+$, $CD5^+$), ZAP-70 and CD38 expression levels were analyzed by flow cytometry and quantified as previously described (Crespo et al., *N Engl J Med*, 348(18), 1764-1775 (2003)). The cut-off point for high expression levels of ZAP-70 was >20% and >30% for CD38 (Hus et al., *Ann Oncol*, 17(4), 683-690 (2006)). All the CLL samples used in this study carried more than 95% of tumoral cells. Cytogenetic alterations were assessed by fluorescence in situ hybridization (FISH) using the multiprobe commercial kit from Vysis (Downers Grove, Ill.), that contains locus-specific probes to determine the deletions of 17p13.1 (p53), 11q22.3 (ATM) and 13q14.3 (D13S319) and a centromeric probe to detect trisomy 12. The mutations of p53 gene are usually missense mutations, and the mutant protein has a prolonged half-life enabling its detection by Western Blot. In addition, p53 mutations were confirmed by direct sequencing according to the IARC TP53 consortium.

Apoptosis Induction

Cells were incubated for different time points with forodesine at doses ranging from 1 to 12 µM in the presence or absence of 10-20-30 µM of deoxyguanosine (dGuo). When indicated, cells were pre-incubated for 1 hour with the pan-caspase inhibitor z-VAD.fmk (benzyloxy-carbonyl-Val-Ala-Asp-fluoro-methylketone; Bachem, Bubendorf, Switzerland) at 80 the caspase-8 inhibitor z-IETD.fmk at 50 µM (Z-Ile-Glu(OMe)Thr-DL-Asp (OMe)-fluoromethylketone, Bachem), 2'-deoxycytidine (5-10-20 µM, Sigma), N-acetyl-L-cysteine (NAC, 25 mM), Tiron (5 mM, 4,5-Dihydroxy-1,3-Benzene-disulfonic acid, Sigma) or GSH (2 mM; Sigma). For the drug combination studies, cells were pretreated for 4, 12 or 24 hours with fludarabine or bendamustine, or 1 hour with the monoclonal antibody anti-CD20 rituximab before adding forodesine (2 µM) plus dGuo (10-20 µM). Cell viability and apoptosis induction was analyzed by changes in cell complexity by means of FSC/SSC, quantification of phosphatidyl serine (PS) exposure by double staining with Annexin-V conjugated to fluorescein isothiocyanate (FITC) and propidium iodide (PI) (Bender-Medsystems, Vienna, Austria). For the analysis of apoptosis in the $CD3^+$ and $CD19^-$ populations, PBMCs were labeled simultaneously with anti-CD3-FITC (Immunotech, Marseille, France), anti-CD19-PE (Becton Dickinson) and Annexin-V-APC. Cell viability and cytotoxicity were plotted as percentage with respect to control cells. Loss of mitochondrial transmembrane potential ($\Delta\Psi m$) were evaluated by staining cells with 20 nM of $DiOC_6$ (3,3-diexyloxacarbocyanine iodide, Molecular Probes) and reactive oxygen species (ROS) production was determined by staining cells with 2 µM dihydroethidine (DHE; Molecular Probes) and flow cytometry analysis. The activation of the pro-apoptotic Bax and Bak proteins due to a conformational change was analyzed by immunocytometry labelling cells with antibodies directed against the NH2-terminal of Bax or Bak proteins as previously described (Bellosillo et al., Blood, 100(5), 1810-1816 (2002)). This region is occluded in basal conditions, and is not available for binding by NH2-terminal epitope-specific antibodies. After apoptotic stimuli, the conformational change of these proteins exposes the NH2-terminus and the hydrophobic COOH-terminus that targets mitochondria, playing an important role in the induction of cell death machinery mediated by mitochondria. In brief, cells were washed once in PBS and fixed in paraformaldehyde 4%, permeabilized with 0.1% saponin and 0.5% bovine serum albumin (BSA). Cells were stained with 1 µg/ml of primary antibodies against conformational active Bak (Oncogene Research), or Bax (clone 6A7, BD Pharmingen) antibodies at room temperature. After several washes in permeabilization buffer, cells were incubated with a secondary goat anti-mouse FITC (DAKO) or goat anti-rabbit FITC (Supertechs) antibody and washed again with permeabilization buffer. Ten thousand stained cells per sample were then analyzed by flow cytometry.

Measurement of Intracellular dGTP Levels $15 \times 10^6$ of CLL primary cells were incubated with or without forodesine (2 µM) and dGuo (10 µM) or fludarabine (1 µg/ml) for 18 hours and the nucleotides were extracted with 60% methanol and intracellular dGTP levels were quantified by DNA polymerase assay as modified by Sherman and Fyfe (Sherman et al., Anal Biochem, 180(2), 222-226 (1989)). Data were expressed in fold induction of intracellular dGTP levels respect of control cells. In parallel, cell viability at 24 and 48 hours were also evaluated.

Immunoblotting

Cells were lysed for 15 min in RIPA buffer supplemented with protease and phosphatase inhibitors (leupeptine 10 µg/ml, apoprotinine 10 µg/ml, 1 µM PMSF, 1 µM sodium ortovanadate, 1 µM NaF, 2 µM sodium pyrophosphate decahydrate (Sigma)). Total cellular proteins were separated by SDS-PAGE under reducing conditions and transferred to Immobilon-P (Millipore) membranes. For protein detection, membranes were probed with the following primary antibodies: anti-Bim, anti-Bak (Ab1) anti-Caspase-8 (Ab-3), anti-p53 (Ab-2) (Calbiochem); anti-Bid, anti-Caspase-9, anti-FoxO1 and anti-XIAP (Cell Signaling Technologies); anti-Bcl-2, anti-dCK, anti-Mcl-1 (S-19) and anti-p73 (clone 5B429) (Santa Cruz Biotechnology); anti-PARP (Roche); anti-Caspase-3 and anti-Bax (clone 6A7) (BD-Pharmingen); anti-survivin (Abcam); anti-β-actin and anti-α-tubulin (Sigma) and anti-FoxO3A (Upstate). Rabbit Anti-phospho dCK (Ser79) and rabbit anti-dCK were a kindly provided by Caroline Smal and Francoise Bontemps (Universite Catholique de Louvain, Belgium). After the incubation with the appropriate primary antibody, the blots were developed with horseradish peroxidase (HRP)-labeled anti-mouse (Sigma), anti-rabbit (Sigma) or anti-goat (Dako) antibodies by using enhanced chemiluminiscence (ECL) reagents (Pierce). Equal protein loading was confirmed with β-actin or α-tubulin expression and relative protein quantification was done with Image Gauge Fujifilm software (Fuji).

mRNA Quantification by Real Time RT-PCR

Total RNA was extracted from $10^7$ cells using the TRIZOL reagent (Invitrogen, Carlsbad, Calif.) according to the manufacturer's instructions. One microgram of total RNA was then retro-transcribed to cDNA using random primers and the M-MLV reverse transcriptase (Invitrogen). The expression levels of p73 and Mcl-1 were determined in an ABI Prism 7900HT Sequence Detection System (Applied Biosystems, Foster City, Calif.) using pre-designed Assay-on-demand (Applied Biosystems). The relative expression of each gene was quantified by the comparative cycle threshold (Ct) method (ΔΔCt), using GUS as an endogenous control. mRNA expression levels were given as arbitrary quantitative PCR units, taking as a calibrator the control sample (untreated) of each case.

Statistical Analysis

Data are represented as mean±standard deviation (SD) of three independent experiments. All statistical analysis was performed using Graphpad Prism 3.0 software (GraphPad Software Inc., San Diego, Calif.). Comparison between two groups of samples was evaluated by non-parametric Mann-Whitney test and correlation coefficients were assessed using Spearman test. Results were considered statistically significant when p-value<0.05 (*p<0.05, p<0.01, *p<0.0001). In order to evaluate the combination effect between two different drugs, the combination index or CI value was analyzed using the algorithm described by Chou and Talalay (Calcusyn software v2.0, Biosoft, Cambridge, UK) (Chou et al., Adv Enzyme Regul, 22, 27-55 (1984)). This CI value is an indicative marker for the antagonistic or synergistic effect for the combination effect of two different drugs. The interaction between two drugs was considered synergistic when CI value was lower than 1, additive when equaled 1, and antagonistic when CI was higher than 1.

A number of embodiments of the invention have been described. Nevertheless, it will be understood that various modifications may be made without departing from the spirit and scope of the invention. Accordingly, other embodiments are within the scope of the following claims. All publications, patents and patent applications cited herein are incorporated herein by reference.

What is claimed:

1. A method of treating a hematologic cancer in a subject comprising the steps of:
    a. administering to the subject an effective amount Forodesine; and
    b. administering to the subject an effective amount of an alkylating agent, wherein the administration of Forodesine and the alkylating agent results in a synergistic effect, wherein the alkylating agent is Bendamustine and the hematologic cancer is resistant to Bendamustine and Fludarabine.

2. The method of claim 1, wherein Forodesine and the alkylating agent are administered concurrently.

3. The method of claim 1, wherein Forodesine and the alkylating agent are administered sequentially.

4. The method of claim 1, wherein the alkylating agent is administered one or more times prior to administration of Forodesine.

5. The method of claim 1, wherein the hematologic cancer is non-Hodgkin's lymphoma, chronic lymphocytic leukemia, or acute lymphoblastic leukemia.

6. The method of claim 1, wherein the hematologic cancer contains a p53 deletion.

* * * * *